(12) United States Patent
Tsubota et al.

(10) Patent No.: US 8,183,822 B2
(45) Date of Patent: May 22, 2012

(54) DIGITAL CASSETTE CHARGING APPARATUS, DIGITAL CASSETTE CHARGING SYSTEM, AND DIGITAL CASSETTE CHARGING METHOD

(75) Inventors: Keiji Tsubota, Kanagawa (JP); Naoyuki Nishino, Kanagawa (JP); Yasunori Ohta, Kanagawa (JP); Yutaka Yoshida, Kanagawa (JP); Shoji Takahashi, Kanagawa (JP); Akihito Bettouyashiki, Kanagawa (JP); Yoshiki Takeoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 322 days.

(21) Appl. No.: 12/433,902

(22) Filed: May 1, 2009

(65) Prior Publication Data
US 2009/0278504 A1 Nov. 12, 2009

(30) Foreign Application Priority Data
May 7, 2008 (JP) ................................ 2008-121361

(51) Int. Cl.
*H02J 7/00* (2006.01)
(52) U.S. Cl. ........................................ 320/106; 320/125
(58) Field of Classification Search .................. 320/106, 320/113, 124–126, 131
See application file for complete search history.

(56) References Cited

U.S. PATENT DOCUMENTS

| 6,980,388 | B2 * | 12/2005 | Ishikawa et al. | 360/75 |
| 7,787,587 | B2 * | 8/2010 | Tasaki | 378/37 |
| 2001/0008373 | A1 * | 7/2001 | Kim | 320/113 |
| 2005/0151505 | A1 * | 7/2005 | Dias et al. | 320/106 |
| 2007/0228680 | A1 * | 10/2007 | Reppert et al. | 280/47.35 |
| 2008/0154744 | A1 * | 6/2008 | Amitani et al. | 705/26 |

FOREIGN PATENT DOCUMENTS

| JP | 7-22709 U | | 4/1995 |
| JP | 11-007159 | * | 1/1999 |
| JP | 2000-206636 | * | 1/1999 |
| JP | 11-146254 A | | 5/1999 |
| JP | 3611084 B2 | | 1/2005 |

* cited by examiner

*Primary Examiner* — Timothy J Dole
*Assistant Examiner* — Alesa Allgood
(74) *Attorney, Agent, or Firm* — SOLARIS Intellectual Property Group, PLLC

(57) ABSTRACT

There is provided a digital cassette charging apparatus including: a charging unit loadable with plural types of digital cassette each comprising a rechargeable battery, the charging unit capable of charging the rechargeable batteries of the plural types of digital cassette at the same time; an identification unit for identifying each of the respective types of the plural digital cassettes that have been loaded in the charging unit; a storage unit stored with a charging profile for each of the digital cassettes, the charging profile representing the charging characteristics of the rechargeable battery; and a control unit for reading out from the storage unit the respective charging profile corresponding to the type of digital cassette identified by the identification unit from the plural types of digital cassette, and for controlling the charging unit based on the respective read-out charging profile.

9 Claims, 15 Drawing Sheets

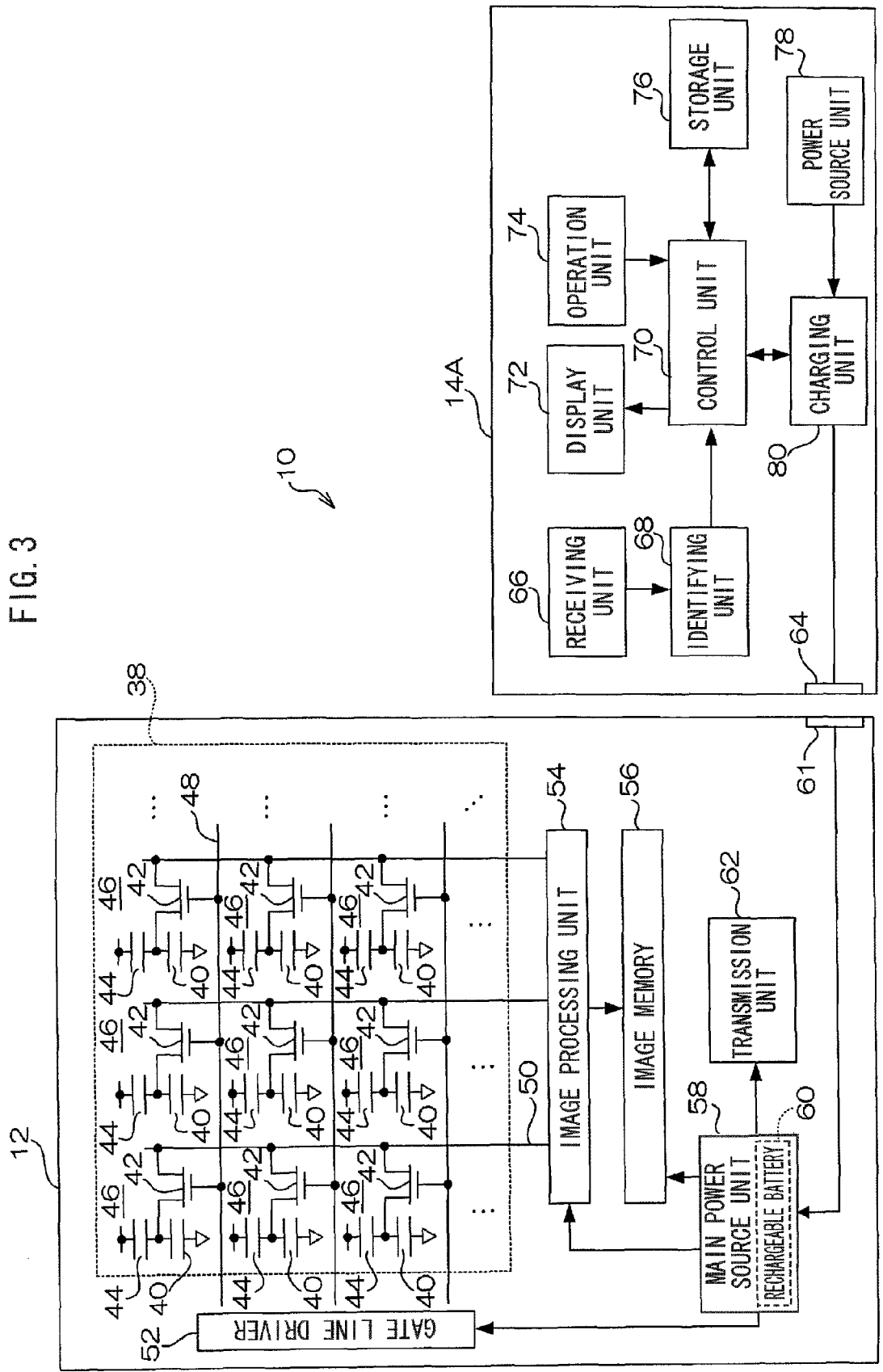

FIG. 5

| TYPE OF DIGITAL CASSETTE | OPTIMUM CHARGING PROFILE OF RECHARGEABLE BATTERY |
|---|---|
| A | CHARGING PROFILE A |
| B | CHARGING PROFILE B |
| ⋮ | ⋮ |

FIG. 12

| TYPE OF DIGITAL CASSETTE | OPTIMUM CHARGING PROFILE OF BATTERY PACK |
|---|---|
| A | 0 ° C CHARGING PROFILE A |
| | 20 ° C CHARGING PROFILE A |
| | 40 ° C CHARGING PROFILE A |
| B | 0 ° C CHARGING PROFILE B |
| | 20 ° C CHARGING PROFILE B |
| | 40 ° C CHARGING PROFILE B |
| ⋮ | ⋮ |

| TYPE OF DIGITAL CASSETTE | MAXIMUM VOLTAGE VALUE | MAXIMUM CURRENT VALUE | CAPACITY |
|---|---|---|---|
| A | 8.4 V | 3430 mA | 1000 mAh |
| B | 8.4 V | 1715 mA | 5000 mAh |
| C | 12.6 V | 3430 mA | 15 000 mAh |
| ⋮ | ⋮ | ⋮ | ⋮ |

DIGITAL CASSETTE CHARGING APPARATUS, DIGITAL CASSETTE CHARGING SYSTEM, AND DIGITAL CASSETTE CHARGING METHOD

CROSS-REFERENCE TO RELATED APPLICATION

This application is based on and claims priority under 35 USC 119 from Japanese Patent Application No. 2008-121361 filed on May 7, 2008.

BACKGROUND

1. Technical Field

The present invention relates to a digital cassette charging apparatus, digital cassette charging system, and digital cassette charging method, and in particular to a digital cassette charging apparatus, digital cassette charging system, and digital cassette charging method capable of charging plural digital cassettes.

2. Related Art

Chargers are known for supplying electrical power to rechargeable batteries in which a single charger charges plural rechargeable batteries or a battery pack in which plural rechargeable batteries are packaged.

As such a method for charging rechargeable batteries etc., a method is known in which plural slots are provided for charging rechargeable batteries etc. of the same shape (Japanese Patent No. 3611084).

In addition, as a method for charging rechargeable batteries etc. that are different from each other, a method is known in which during the period in which one rechargeable battery etc. is being charged another rechargeable battery etc. cannot be loaded (Japanese Patent Application Laid-Open (JP-A) No. 11-146254).

A method is also known for charging plural of the same type of rechargeable batteries etc. at the same time (Japanese Utility Model Application Laid-Open No. 7-22709).

However, in the technology of Japanese Patent No. 3611084, since plural slots of the same shape are provided, the rechargeable batteries etc. that can be loaded therein must also be of the same type.

In the technology of JP-A No. 11-146254 rechargeable batteries etc. with different charging voltages cannot be charged at the same time.

In addition, in the technology of Japanese Utility Model Application Laid-Open No. 7-22709, while plural rechargeable batteries etc. can be charged at the same time, the rechargeable batteries etc. for charging must be of the same type.

SUMMARY

The present invention addresses the above issues, and an objective thereof is to provide a digital cassette charging apparatus, digital cassette charging system, and digital cassette charging method capable of charging plural types of electrical storage device, e.g., rechargeable battery, and the like at the same time.

In order to achieve the above objective, an aspect of the present invention provides a digital cassette charging apparatus including:

a charging unit loadable with a plurality of types of digital cassette each comprising an electrical storage device including a rechargeable battery or a capacitor, the charging unit capable of charging the electrical storage devices of the plurality of types of digital cassette at the same time;

an identification unit for identifying each of the respective types of the plurality of digital cassettes that have been loaded in the charging unit;

a storage unit stored with a charging profile for each of the digital cassettes, the charging profile representing the charging characteristics of the electrical storage device; and a control unit for reading out from the storage unit the respective charging profile corresponding to the type of digital cassette identified by the identification unit from the plurality of types of digital cassette, and for controlling the charging unit based on the respective read-out charging profile.

Here, the capacitor may includes an electric field capacitor, an electric double-layer capacitor, or a lithium ion capacitor, and the like.

According to the aspect of the present invention, plural types of digital cassette having an electrical storage device, e.g., a rechargeable battery, are loadable and the electrical storage devices of the plural types of digital cassette can be charged at the same time by using the charging unit, the respective type of digital cassette can be identified from the plural digital cassettes loaded in the charging unit by using the identification unit, and a charging profile for each of the digital cassettes, representing the charging characteristics of the electrical storage device, can be stored by using the storage unit.

In addition, in the present invention, the electrical storage device charging profile corresponding to the digital cassette(s) identified by the identification unit can be read out from the storage unit, and the charging unit can be controlled based on the charging profile by using the control unit.

In this manner, according to the aspect of the present invention, plural types of electrical storage device can be charged at the same time, since each of the respective types of plural loaded digital cassettes are identified, charging profiles representing the charging characteristics of the electrical storage devices are stored for each of the digital cassettes, and the charging amount is controlled based on the charging profile(s) corresponding to the identified plural digital cassettes.

A barcode indicating the type of the digital cassette may be adhered to the digital cassette, and the identification unit may comprise a read-out unit for reading out the barcode, and the identification unit may identify each of the respective types of digital cassette from the plurality of types of digital cassette based on information of the read-out barcode.

The charging unit may comprise a connection portion shaped to correspond to the plurality of digital cassettes, and the identification unit may identify each of the respective types of digital cassette from the plurality of types of digital cassette by detecting the digital cassette connected to the connection portion.

The charging unit may comprise plural charging electrodes, the identification unit may comprise a contact pattern detection portion for detecting a contact pattern between a charging electrode of the digital cassette and the charging electrodes, and the identification unit may identify each of the respective types of digital cassette based on the detected contact pattern.

The digital cassette may be provided with a transmission unit for transmitting digital cassette information representing the type of the digital cassette; and the identification unit may identify each of the respective types of digital cassettes loaded into the charging unit based on the digital cassette information transmitted from the transmission unit.

The charging profile may comprise: information determined for each of the electrical storage devices of a maximum voltage value, maximum current value, and capacity during charging; and a basic charging profile determined in advance.

The digital cassette charging apparatus may further comprise:

a temperature detecting unit for detecting temperature, and charging profiles are stored in the storage unit for each of the digital cassettes, the charging profiles representing charging characteristics for each of a plurality of temperatures of the electrical storage device, wherein the control unit reads out from storage unit each of the respective charging profiles corresponding to the type of digital cassette identified by the identification unit from the plurality of types of digital cassette and corresponding to the temperature detected by the temperature detecting unit, and the control unit controls the charging unit based on each of the respective read-out charging profiles.

In order to achieve the above objectives, another aspect of the present invention provides a digital cassette charging system including:

a plurality of types of digital cassette; and a digital cassette charging apparatus for loading with the plurality of types of digital cassette and charging the digital cassettes at the same time, wherein the digital cassette charging apparatus comprises:

a charging unit loadable with a plurality of types of digital cassette each comprising an electrical storage device including a rechargeable battery or a capacitor, the charging unit capable of charging the electrical storage devices of the plurality of types of digital cassette at the same time;

an identification unit for identifying each of the respective types of the plurality of digital cassettes loaded in the charging unit;

a storage unit stored with a charging profile for each of the digital cassettes, the charging profile representing the charging characteristics of the electrical storage device; and a control unit for reading out from the storage unit each of the respective charging profiles corresponding to the types of digital cassette identified by the identification unit from the plurality of types of digital cassette, and for controlling the charging unit based on each of the respective read-out charging profiles.

According to this aspect of the invention plural types of rechargeable battery etc. can be charged at the same time.

In addition, in order to achieve the above objectives, still another aspect of the present invention provides a digital cassette charging method including:

identifying each of respective types of a plurality of digital cassettes loaded in a charging unit loadable with a plurality of types of digital cassette each comprising an electrical storage device including a rechargeable battery or a capacitor, the charging unit capable of charging the electrical storage devices of the plurality of types of digital cassette at the same time;

reading out each respective charging profile corresponding to the identified types of digital cassette from the plurality of digital cassettes, reading out being from a storage unit in which a charging profile representing the charging characteristics of the electrical storage device has been stored for each of the electrical storage devices of the plurality of digital cassettes; and controlling the charging unit based on each of the respective read-out charging profiles.

According to this invention plural types of rechargeable battery or the like can be charged at the same time.

An effect that plural types of rechargeable battery or the like can be charged at the same time is obtained according to the present invention.

BRIEF DESCRIPTION OF THE DRAWINGS

Exemplary embodiments of the present invention will be described in detail based on the following figures, wherein:

FIG. 3 is a block diagram showing a schematic configuration of a layout of a digital cassette and a digital cassette charging apparatus according to a first exemplary embodiment of the present invention;

FIG. 5 is a schematic diagram showing types of digital cassette according to the first exemplary embodiment and an example of data structure for corresponding charging profiles;

FIG. 12 is a schematic diagram showing types of digital cassette according to the fourth exemplary embodiment and an example of data structure for corresponding charging profiles;

DETAILED DESCRIPTION

Explanation will now be given of details of a first exemplary embodiment of the present invention.

Figure 1:
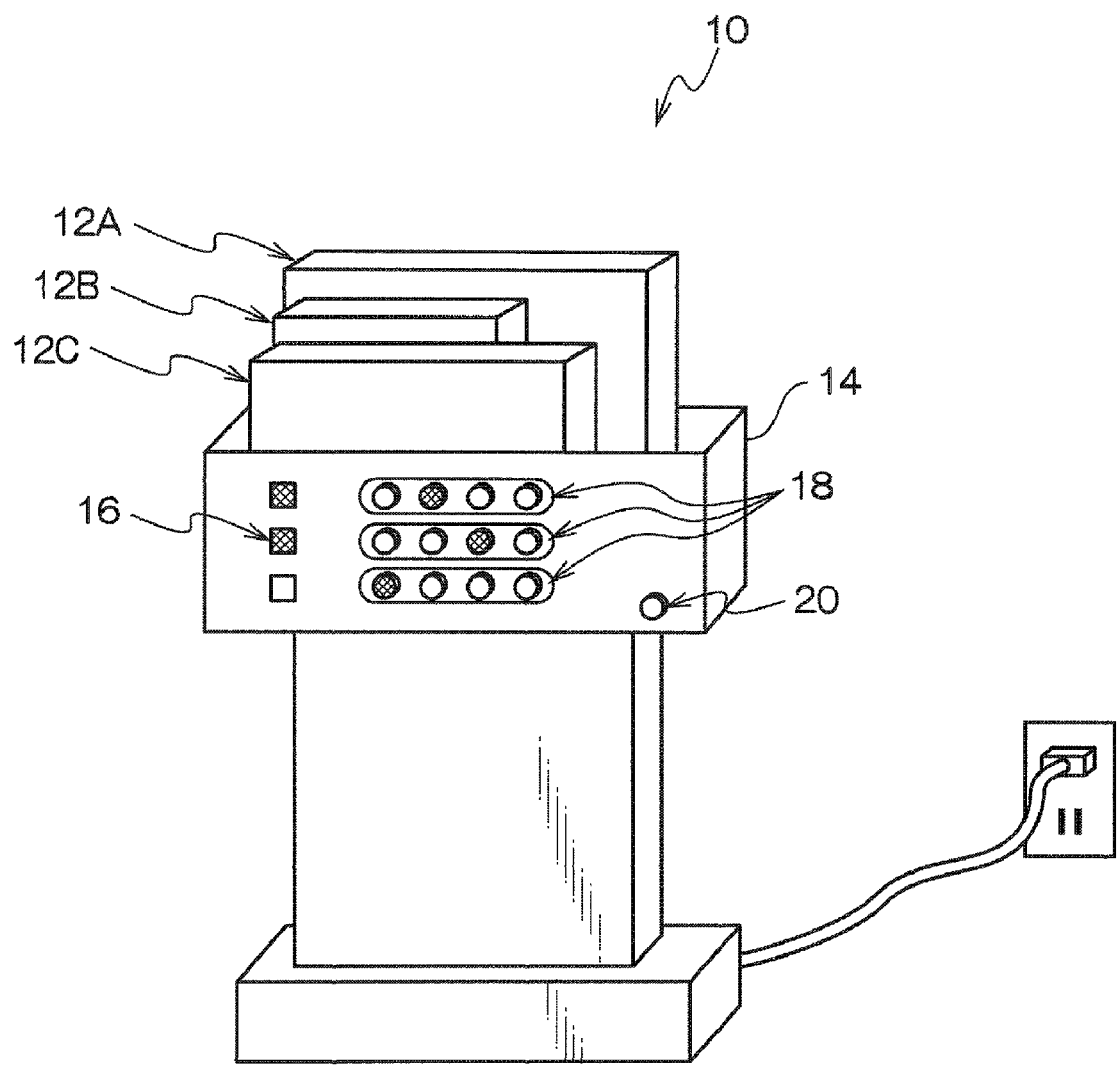
FIG. 1 is a schematic diagram of a digital cassette charging system according to an exemplary embodiment of the present invention.

As shown in FIG. 1, a digital cassette charging system 10 according to a first exemplary embodiment of the present invention is configured with: plural types of portable digital cassettes 12A to 12C that are capable of converting, into image data, image information carried by radiation each time the digital cassettes 12A to 12C are irradiated, and accumulating and storing the image data; and a digital cassette charging apparatus (referred to below simply as charging apparatus) 14, for accommodating and charging the accommodated plural types of the digital cassettes 12A to 12C. The charging apparatus 14 is capable of being loaded with, and charging, the plural types of the digital cassettes 12A to 12C at the same time.

The charging apparatus 14 is also provided with the charging state LEDs 16 that show the charging state, charging mode display LEDs 18 that shown the charging mode, and a charging start button 20 for starting charging.

Note that while there are the three digital cassettes 12A to 12C shown loaded in FIG. 1, the number of digital cassettes are not limitation thereto. Also, when the explanation below is not particularly limited to one or other of the digital cassettes 12A to 12C, reference will simply be made to "digital cassette 12".

Figure 2A:
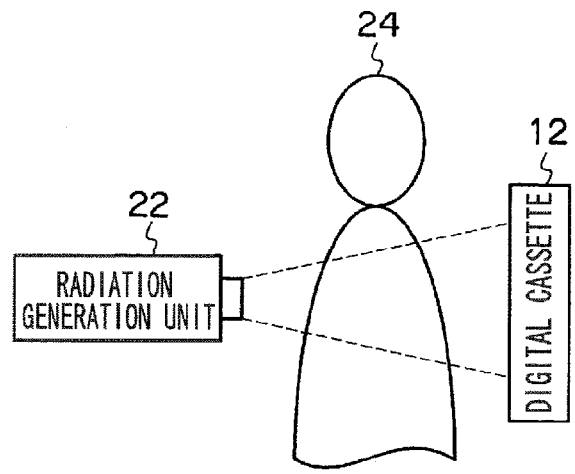
FIG. 2A is a schematic diagram showing a disposition of a digital cassette during radiographic image capture.

When capturing radiographic images, the digital cassette 12 is placed with a separation to a radiation generation unit 22 that generates radiation, such as X-rays, as shown in FIG. 2A. An imaging position for positioning an imaging subject 24 is present between the radiation generation unit 22 and the digital cassette 12. When capture of a radiographic image is instructed, the radiation generation unit 22 emits radiation of a radiation amount, in accordance with preset imaging conditions or the like. The radiation radiated from the radiation generation unit 22 picks up image information by transmission through the imaging subject 24 positioned at the imaging position, and this radiation is then irradiated onto the digital cassette 12.

Figure 2B:
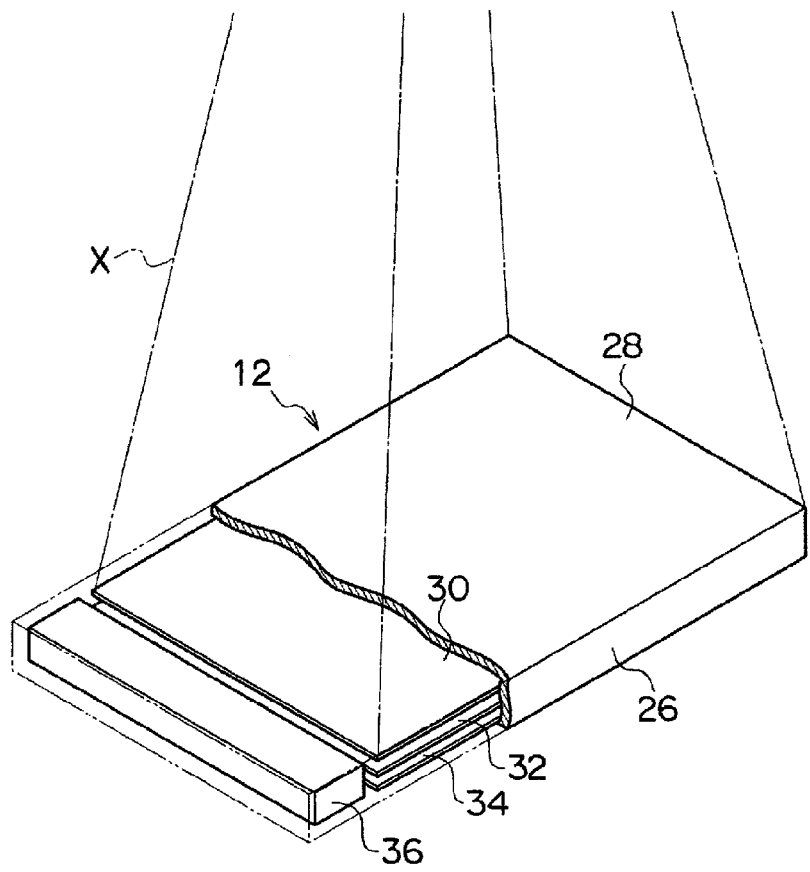
FIG. 2B is a perspective view showing the internal structure of a digital cassette.

The digital cassette 12 is covered by a rectangular flat plate-shaped casing (case) 26 formed of a thickness of material such that X-rays can be transmitted therethrough, as shown in FIG. 2B. Within the casing 26 are disposed, in sequence from an irradiation face 28 of the casing 26 onto which the X-rays are irradiated, a grid 30 for removing any scattered X-rays generated due to transmission through the imaging subject 24, a radiation detector (radiation detection panel) 32 for detecting X-rays, and a lead plate 34 for absorbing back-scattering X-rays. It should be noted that the irradiation face 28 of the casing 26 may be configured by the grid 30, and the grid 30 may be disposed outside the irradiation face 28. In addition a case 36 for housing a microcomputer containing various circuits (described later) is disposed at one end within the casing 26. It is also preferable to dispose a lead plate or the like at the irradiation face 28 side of the case 36 in order to avoid the various circuits within the case 36 being damaged during irradiation with X-rays.

Explanation will now be given of the configuration of the electrical systems of the digital cassette 12 and the charging apparatus 14.

The radiation detector 32 of the digital cassette 12 is configured with a TFT active matrix board 38, as shown in FIG. 3, layered thereon with an X-ray-charge converting material for absorbing radiation and converting it into charge. The X-ray-charge converting material is formed with, for example, selenium as a main component thereof (for example contained at a proportion of 50% or above) using non-crystalline a-Se (amorphous selenium). When radiation is irradiated onto the X-ray-charge converting material, the X-ray-charge converting material converts irradiated radiation into charge by internally generating charge (electron-hole pair) of an amount of electric charge in accordance with the amount of irradiated radiation. A fluorescent material and photoelectric conversion element (photodiode) may be used in place of the X-ray-charge converting material like a-Se. A gadolinium oxysulfide compounds (GOS) and cesium iodide (CsI) are well known as fluorescent materials. In such cases conversion of X-rays to charge becomes possible, similar to when an X-ray-charge converting material is used, by combining X-ray-light conversion in the fluorescent material and using a photodiode photoelectric conversion element to perform photoelectric conversion.

Plural individual pixel portions 46 are disposed in a matrix shape on the TFT active matrix board 38. Each of the pixel portions 46 is provided with an individual storage capacitor 40 for accumulating charge generated in the X-ray-charge conversion layer and/or photoelectric conversion layer, and a TFT 42 for reading out the charge accumulated in the storage capacitor 40. In FIG. 3 an X-ray-charge conversion layer corresponding to individual pixel portions 46 is shown pictorially as X-ray-charge conversion portions 44. The charge generated in the X-ray-charge conversion layer, by irradiation of the digital cassette 12 with radiation, is accumulated in the respective storage capacitor 40 of the individual pixel portions 46. In this manner, the image-information carried in the radiation irradiated onto the digital cassette 12 is converted into charge information, and held in the radiation detector 32.

The TFT active matrix board 38 is provided with plural gate lines 48 extending along a fixed direction (row direction) for switching on and off the TFT 42 of the individual pixel portions 46, and is provided with plural data lines 50 extending in a direction perpendicular to the gate lines 48 (column direction) for reading out accumulated charge from the storage capacitors 40 through the TFTs 42 that are switched on. Individual gate lines 48 are connected to a gate line driver 52, and individual data lines 50 are connected to an image processing unit 54. When charge has been accumulated in the storage capacitor 40 of individual pixel portions 46, the TFTs 42 of the individual pixels 40 are switched on in sequence of single row units by a signal supplied from the gate line driver 52 through the gate lines 48, and the charge that has been accumulated in the storage capacitor 40 of the pixel portions 46 for which the TFT 42 is on, is transmitted as a charge signal through the data lines 50 and input to the image processing unit 54. The charge that has been accumulated in the storage capacitors 40 of individual pixel portions 46 is consequently read out in sequence in single row units.

While not illustrated in the figures, the image processing unit 54 is provided with an amplifier and a sample and hold circuit for each of the individual data lines 50. After the charge signal transmitted through the data line 50 has been amplified by the amplifier it is then held in the sample and hold circuit. A multiplexer and an A/D convertor are connected in sequence to the output side of the sample and hold circuits, and the charge signals held in the individual sample and hold circuits are input in sequence (serially) into the multiplexer, and converted into digital image data by the A/D convertor. There is an image memory 56 connected to the image processing unit 54, and image data output from the A/D convertor of the image processing unit 54 is stored in sequence in the image memory 56. The image memory 56 has a capacity capable of storing image data equivalent to that from plural lines up to that from plural films, and each time radiographic imaging is performed the image data obtained by imaging is stored in sequence in the image memory 56.

A main power source unit 58 is provided to the digital cassette 12. A rechargeable battery 60 (battery) that can be charged is installed in the main power source unit 58 so that the portability of the digital cassette 12 is not compromised. A lithium ion battery or the like can be used, for example, as the rechargeable battery 60. The rechargeable battery 60 may also be configured from a single rechargeable battery, or may be configured from a battery pack in which plural rechargeable batteries have been packaged.

A rechargeable battery electrode 61 is provided to the digital cassette 12. The rechargeable battery 60 is charged by power supplied from the charging apparatus 14 by loading the digital cassette 12 in the charging apparatus 14, and the rechargeable battery electrode 61 making contact with an electrode 64 provided to the charging apparatus 14. Note that, while not shown in FIG. 3, the electrode 64 is configured from plural electrodes having an appropriate permitted current capacity according to the size of the charging current of the rechargeable battery installed in the digital cassette 12.

The main power source unit 58 supplies power from the charged rechargeable battery 60 to various circuits and elements (the gate line driver 52, image processing unit 54, image memory 56 etc.), and the various circuits and various elements are operated by the power supplied.

The TFT active matrix board 38 generates charge, of a charge amount according to the amount of irradiated radiation, by power supplied from the main power source unit 58.

A transmission unit 62 is connected to the main power source unit 58. The transmission unit 62 has information for identifying the type of digital cassette 12 stored in a non-illustrated internal memory. This information includes information, for example in the case of the digital cassette 12A, indicating the digital cassette 12A. When, for example, the digital cassette 12 is loaded in the charging apparatus 14, starting charging is instructed by a user, and transmission of information indicating the type of digital cassette is requested by the charging apparatus 14, the transmission unit 62 reads out in the information stored in its internal memory indicating the type of digital cassette and transmits this information.

Explanation will now be given of the charging apparatus 14. The charging apparatus 14 according to the first exemplary embodiment is taken below as being the charging apparatus 14A. A power source unit 78 is provided to the charging apparatus 14A. The power source unit 78 is, for example, connectable to a commercial power supply, and converts alternating current supplied from the commercial power source to direct current, and alternating voltage into direct voltage, before supplying power to the various circuits and elements within the charging apparatus 14 (controller 70, receiving unit 66, identifying unit 68, storage unit 76, display unit 72, etc.). The various circuits and various elements are operated by power supplied from the power source unit 78.

When the digital cassette 12 is loaded in the charging apparatus 14A and the rechargeable battery electrode 61 makes contact with the electrode 64 and enters a conductive state, the charging unit 80 charges the rechargeable battery 60 of the main power source unit 58 through the electrode 64 and the rechargeable battery electrode 61. The charging unit 80 also has functionality for detecting the capacity of the charging current of the rechargeable battery 60 when the electrode 64 and the rechargeable battery electrode 61 are in a state of contact, and for outputting the capacity detected to the controller 70. The receiving unit 66 receives information transmitted from the digital cassette 12 indicating the type of digital cassette 12. Examples of methods used as the transmission method for this information include methods capable of reading in and reading out information such as wireless methods using RFID (Radio Frequency IDentification) tags, wireless communication such as by infrared communication and wireless LAN etc., and wired communication using a connector.

For example, when a method using an RFID tag is employed, configuration can be made with information indicating the type of digital cassette 12 stored as an RFID tag, with a read-out unit reading out of the information stored on the RFID tag, indicating the type of digital cassette 12.

The identifying unit 68 identifies the type of digital cassette 12 based on the information received by the receiving unit 66. A table showing correspondence relationships, between the information of the signal sent from the transmission unit 62 and the type of digital cassette 12, is stored in advance in a non-illustrated internal memory of the identifying unit 68. The type of digital cassette 12 is determined based on the information transmitted from the transmission unit 62.

Information showing correspondence relationships, between the type of digital cassette 12 and the charging profile (described later), representing the charging characteristics corresponding to the types of digital cassette 12, is stored in advance in the storage unit 76.

The controller 70 reads out from the storage unit 76 the charging profile information corresponding to the type of digital cassette loaded in the charging apparatus 14, as input by the identifying unit 68, and the controller 70 controls the voltage value of the charging voltage, and the current value of the charging current, for the charging unit 80 to charge the rechargeable battery 60, based on the read-out charging profile information.

The charging unit 80 appropriately converts the direct current and voltage supplied from the power source unit 78, such that the rechargeable battery 60 is charged with the voltage value and current value of the charging current and voltage instructed by the controller 70, and supplies power to the rechargeable battery 60.

The display unit 72 is configured to include the above charging state LEDs 16 and charging mode display LEDs 18. The charging state LEDs 16 display the charging state of the rechargeable battery 60 of the loaded digital cassette 12. For example, the charging state LEDs 16 are lit with a blue light when the rechargeable battery 60 is sufficiently charged for operation of the digital cassette 12, and are lit with a red light when the rechargeable battery 60 is not sufficiently charged.

The charging mode display LEDs 18 are configured to include plural LEDs as shown in FIG. 1, such that the approximate charging duration can be determined by the number of LEDs that are lit.

The operation unit 74 is configured to include a charging start button 20 for operation by a user to start charging. Note that configuration may be made omitting the charging start button 20, with the charging apparatus 14 automatically identifying that the digital cassette 12 is loaded in the charging apparatus 14, and charging starting automatically.

Explanation will now be given of charging profiles, with reference to FIG. 4.

Figure 4:
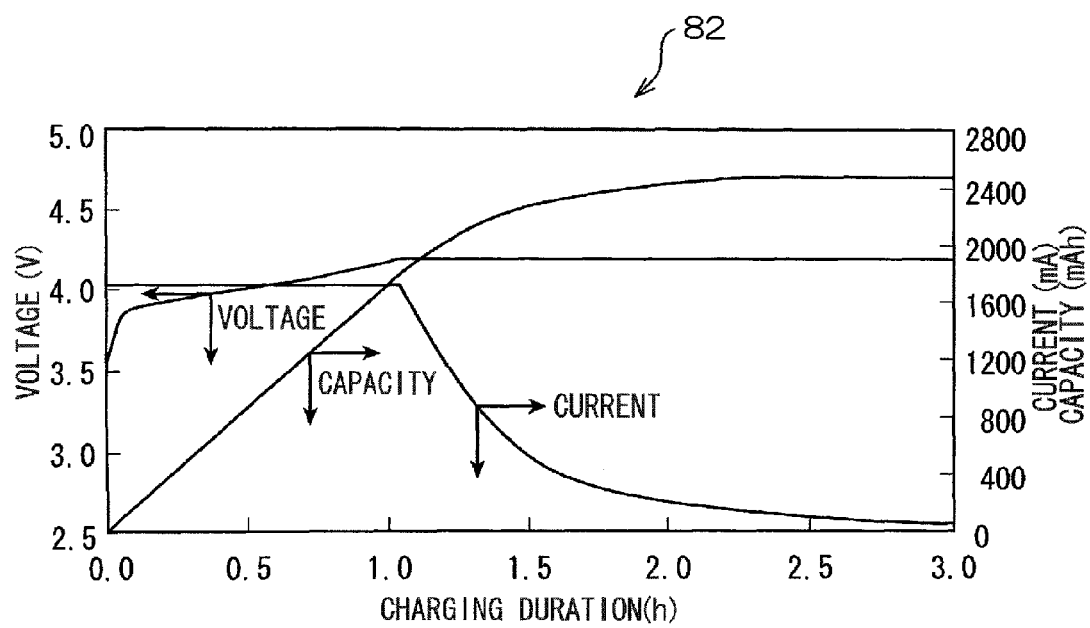
FIG. 4 is a schematic diagram showing a charging profile.

FIG. 4 is a schematic diagram showing a charging profile 82, representing the charging characteristics of a lithium ion battery X, one example of the rechargeable battery 60.

A charging profile is a profile representing the relationship against charging duration for various voltage values of charging voltage, current values of charging current, and capacities of charging current, these being optimum for charging the rechargeable battery 60 of the digital cassette 12 that is in the loaded state in the charging apparatus 14.

Charging can be performed that is optimum for the rechargeable battery by using the charging profile 82, so as to charge the rechargeable battery 60 with voltage values and current values according to the charging characteristics of the rechargeable battery 60, with the voltage value and current value corresponding to the capacity at the time of loading the rechargeable battery 60.

For example, in the charging profile 82 shown in FIG. 4, if the capacity of the battery X when the digital cassette 12 is loaded is about 2000 mAh, then the voltage required to reach the full charge capacity (about 2500 mAh) is a constant about 4.2 V. It can be seen that the charging current required in the same circumstances starts at about 1400 mAh and is a charging current that drops off with time along the curved line of current in the charging profile.

The charging profile 82 differs according to the configuration of rechargeable batteries loaded in the digital cassette 12.

Namely, for example, even though the same type of rechargeable battery may be used for battery packs, the charging profile of a battery pack in which two rechargeable batteries are connected in series has different characteristics to the charging profile of a battery pack in which two rechargeable batteries are connected in parallel.

In the case of a battery pack in which rechargeable batteries are connected in series, the voltage value required for charging this battery pack is a voltage value that is the product of the voltage value required for a single rechargeable battery multiplied by the number of rechargeable batteries connected in series, with the current value required for charging the battery pack being the same as the current value for a single rechargeable battery.

However, in the case of a battery pack in which rechargeable batteries are connected in parallel, the current value required for charging this battery pack is a current value that is the product of the current value required for a single rechargeable battery multiplied by the number of rechargeable batteries connected in parallel, with the voltage value required for charging the battery pack being the same as the voltage value for a single rechargeable battery.

The characteristics of the charging profile 82 vary in this manner depending on the configuration of the rechargeable batteries, such as the number of rechargeable batteries loaded in the battery pack, whether they are connected in parallel or in series, or whether connected both in series and in parallel. The characteristics of the charging profile 82 also vary depending on type of rechargeable battery.

Explanation will now be given of information 84 stored in the storage unit 76 of the charging apparatus 14A, with reference to FIG. 5. The information 84, as shown in FIG. 5, representing the correspondence relationships between the type of digital cassette and the charging profile information corresponding thereto, is stored in advance in the storage unit 76.

For example, if the type of digital cassette 12A is "A", the controller 70 reads out the charging profile A from the storage unit 76, and controls the charging unit 80 charging the rechargeable battery 60 to be charged on the basis of the read-out charging profile A.

Explanation will now be given of a processing routine for charging processing executed in the charging apparatus 14A, with reference to FIG. 6.

Determination is first made by the controller 70 at step 100 as to whether or not the charging start button 20 has been depressed by a user.

If determination is made at step 100 that the charging start button 20 has been depressed, then the routine proceeds to step 102, and processing for transmitting and receiving information about the digital cassette 12, for identifying the type of digital cassette 12, is performed. Specifically, when the charging start button 20 is depressed, for example, the receiving unit 66 sends a request signal requesting transmission of information representing the type of digital cassette 12, and after receiving the information representing the type of digital cassette 12, transmitted from the transmission unit 62 of the digital cassette 12 in response to the request signal, the receiving unit 66 inputs the received information to the identifying unit 68. When there are plural digital cassettes 12 loaded in the charging apparatus 14A, since information is transmitted representing the type of digital cassette 12 from each of the transmission units 62 provided to the respective digital cassettes 12, the receiving unit 66 receives all of the received information and outputs all the information to the identifying unit 68.

Next, at step 104, the controller 70 determines whether or not the type of the digital cassette 12 loaded in the charging apparatus 14A has been identified. When there are plural loaded digital cassettes 12, then determination is made as to whether or not each of the respective types of digital cassette 12 has been identified.

When it is determined at step 104 that the type of the digital cassette 12 loaded in the charging apparatus 14A has been identified, then at step 106 the optimum charging profile, corresponding to the type of digital cassette 12 identified at step 104, is read out from the storage unit 76. If there are plural digital cassettes 12 loaded then each of the respective optimum charging profiles, corresponding to the digital cassettes 12, is read out from the storage unit 76. The charging unit 80 is instructed to detect the present capacity of the rechargeable battery 60 of the digital cassette(s) 12 and the detected capacity is input from the charging unit 80.

Next, at step 108, the controller 70 decides on the voltage value and charging voltage at the start of charging, based on the read-out optimum charging profile and the detected present capacity of the rechargeable battery 60, and controls the charging unit 80 so as to start supply of charging current to the electrode 64 that is in contact with the rechargeable battery electrode 61 of the loaded digital cassette 12. The controller 70 then controls the voltage value and charging voltage based on the charging profile up until full charge of the rechargeable battery 60 is reached. If there are plural digital cassettes 12 in a loaded state then each of the rechargeable batteries 60 are charged based on present capacity of each of the rechargeable batteries 60 and on the optimum charging profile of each of the rechargeable batteries 60.

When, however, determination is made at step 104 that the type of the loaded digital cassette 12 cannot be identified, for example if an unidentifiable digital cassette 12 is loaded, then the routine proceeds to step 110, charging is not performed, and error display is performed, such as causing the charging state LEDs 16 to flash in red.

As explained above, according to the digital cassette charging system 10 of the first exemplary embodiment, plural types of digital cassette 12 are loadable at the same time, and charging of plural types of rechargeable battery can be performed at the same time since charging profiles are stored in advance corresponding to the rechargeable batteries for plural types of digital cassette 12.

Explanation will now be given of a second exemplary embodiment.

Similar parts of the present exemplary embodiment to that of the first exemplary embodiment are allocated the same reference numerals and explanation thereof is omitted. The charging apparatus 14 according to the second exemplary embodiment is shown as charging apparatus 14B.

Figure 7:
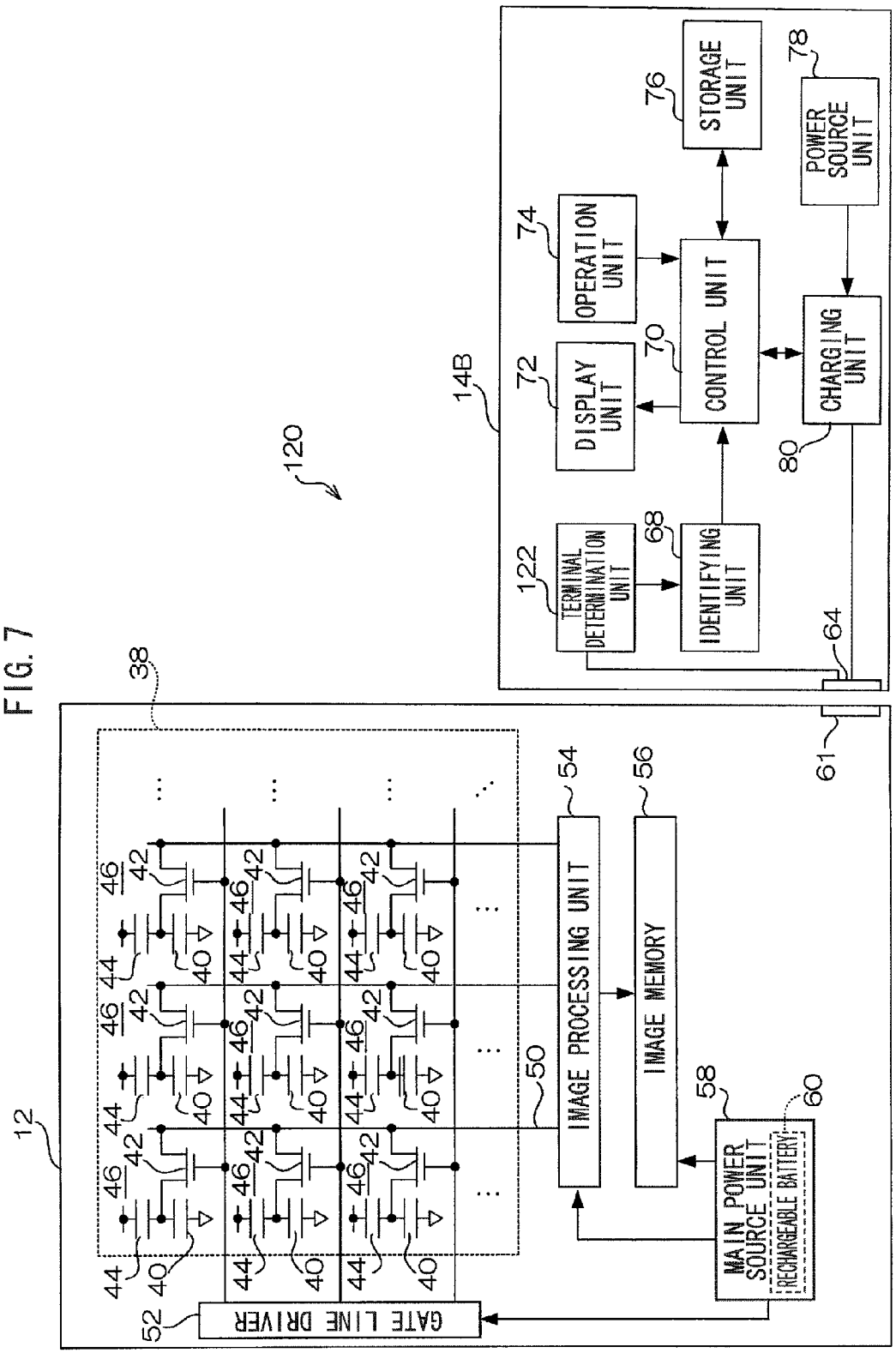
FIG. 7 is a block diagram showing a schematic configuration of a layout of a digital cassette and a digital cassette charging apparatus according to a second exemplary embodiment of the present invention.

The digital cassette charging system 120 according to the present exemplary embodiment, shown in FIG. 7, differs from the digital cassette charging system 10 shown in FIG. 3 in that the transmission unit 62 of the digital cassette 12 thereof is omitted, and a terminal determination unit 122 is provided in the charging apparatus 14B, in place of the receiving unit 66.

Figure 8A:
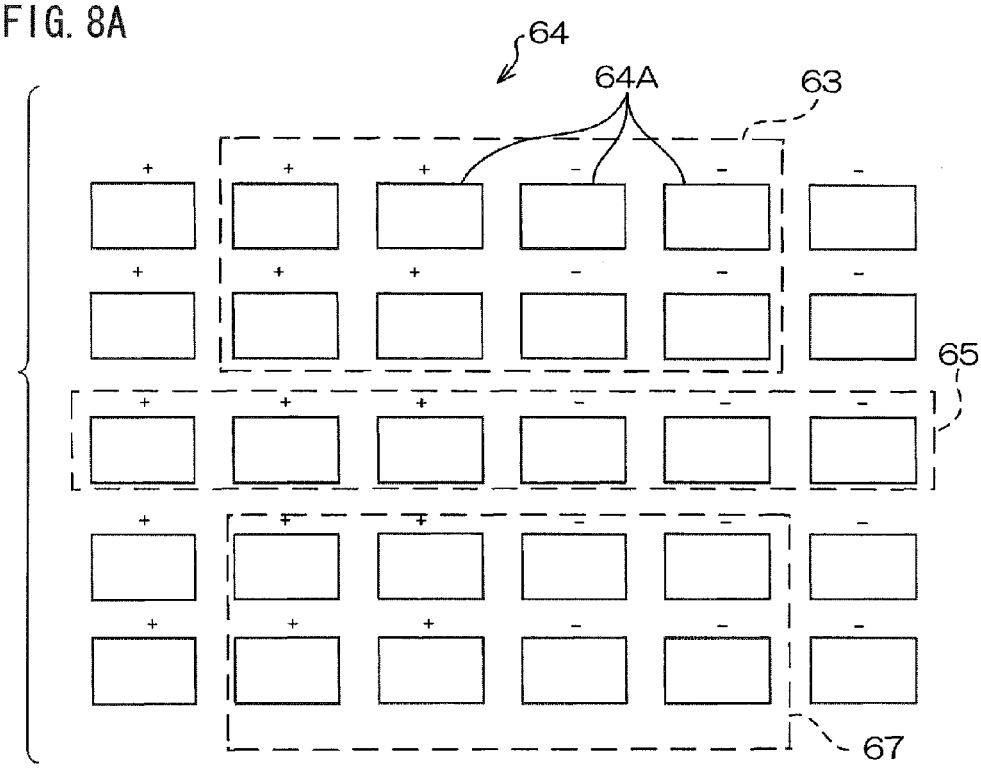
FIG. 8A is a diagram showing a schematic diagram of terminals when the shape of terminals is determined, and in particular is a diagram showing electrodes for charging of a charging apparatus.
Figure 8B:
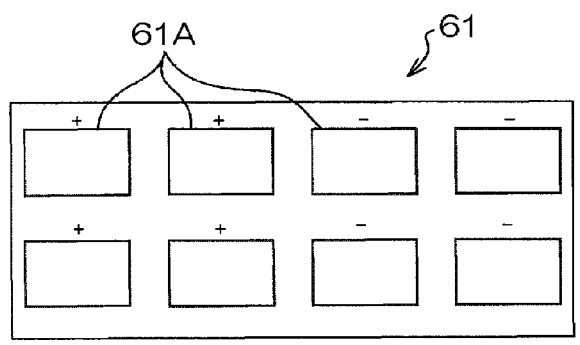
FIG. 8B is a diagram showing a schematic diagram of terminals when the shape of terminals is determined, and in particular is a diagram showing electrodes for the rechargeable battery of the digital cassette 12A shown in FIG. 1.
Figure 8C:
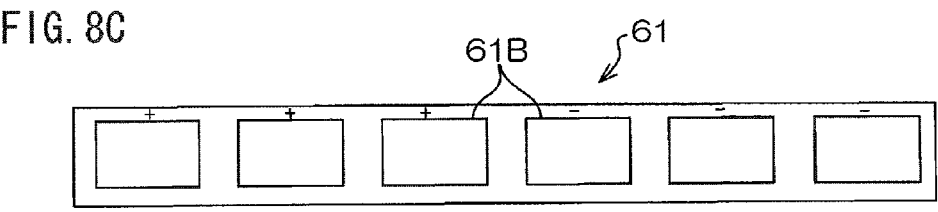
FIG. 8C is a diagram showing a schematic diagram of terminals when the shape of terminals is determined, and in particular is a diagram showing electrodes for the rechargeable battery of the digital cassette 12B shown in FIG. 1.

The electrode 64 of the charging apparatus 14B is formed, for example, from plural electrodes 64A, each of the same shape, as shown in FIG. 8A, and the electrodes 64A are disposed with even spacing between each of the electrodes 64A. In the case of the digital cassette 12A, the rechargeable battery electrode 61 is also formed, for example, of plural electrodes 61A each of the same shape as the electrodes 64A, as shown in FIG. 8B, with the plural electrodes 61A being disposed with the same even spacing therebetween as the electrodes 64A. In the case of the digital cassette 12B, for example as shown in FIG. 8C, the rechargeable battery electrode 61 is formed from plural electrodes 61B each of the same shape as the electrodes 64A, and the electrodes 61B are disposed with the same even spacing between as the electrodes 64A. Note that an example is shown in FIGS. 8A to 8C in which the electrodes are disposed such that positive electrodes and negative electrodes are divided with a boundary line at the center, however the layout is not limited to such a mode.

The terminal determination unit 122 detects the pattern of contact between the electrode 64 and the rechargeable battery electrode 61 of the digital cassette 12, for example in a case where the rechargeable battery electrode 61 is that shown in FIG. 8B, the terminal determination unit 122 detects which of the electrodes 64A is in contact with which of the electrodes 61A. Determination as to whether or not electrodes are in contact with each other may be made, for example, by detection by providing a switch for each of the respective electrodes 64A that is switched one when in contact with the rechargeable battery electrode 61, however there is no limitation thereto.

The terminal determination unit 122 outputs information related to the contact pattern detected to the identifying unit 68.

The identifying unit 68 has, for example, information stored in a non-illustrated internal memory representing the correspondence relationships between the type of digital cassette and contact patterns, and identifies the type of digital cassette corresponding to the contact pattern represented by the information of the contact pattern input from the terminal determination unit 122.

Note that, for example, the electrode 64 on the charging apparatus 14B side and the rechargeable battery electrode 61 on the digital cassette 12 side may each be provided with a groove at a position equivalent to the boundary of the positive electrode side and negative electrode side, so as to align the central position of the electrode of the loaded digital cassette 12.

In such cases, for example, when the detected contact pattern is that of the contact pattern 63 shown in FIG. 8A, then the type of digital cassette that has been loaded can be identified as being the digital cassette 12A in which the plural electrodes 61A are disposed as shown in FIG. 8B. If the detected contact pattern is the contact pattern 65 shown in FIG. 8A, then the type of digital cassette that has been loaded can be identified as being the digital cassette 12C in which the plural electrodes 61B are disposed as shown in FIG. 8C. Also, when the contact pattern is the contact pattern 67 shown in FIG. 8A, then the type of digital cassette that has been loaded can be identified as being the digital cassette 12A. By configuration of the electrode 64 on the charging apparatus 14B side by placement of the plural electrodes 64A the degrees of freedom for positioning the loaded digital cassette can be increased.

In the processing routine of the charging processing according to the present exemplary embodiment, only the processing performed at step 102 to identify the type of digital cassette 12 differs from the processing of the first exemplary embodiment, and the other processing is similar to that of the first exemplary embodiment and explanation thereof will be omitted.

At step 102 the contact pattern, between the rechargeable battery electrode 61 of the digital cassette 12 and the electrode 64 of the charging apparatus 14B, is detected by the terminal determination unit 122 and output to the identifying unit 68. The identifying unit 68 then identifies the type of digital cassette corresponding to the contact pattern represented in the contact pattern information input from the terminal determination unit 122, based on the correspondence relationships of the type of digital cassettes to the contact patterns, stored in a non-illustrated internal memory.

Another method for identifying the type of digital cassette 12 may be used, other than the above method, such as identifying the shape of the bottom face portion, to which the rechargeable battery electrode 61 of the digital cassette 12 is provided.

In such cases the connection portion of the charging apparatus 14B with the digital cassette (the portion where the respective electrodes are in mutual contact) is configured by providing plural types of connection portion shape according to the shapes of the bottom face portions, the shapes differing according to the type of digital cassette. The type of digital cassette can then be identified by detecting which connection portion has been contacted by the digital cassette.

Explanation will now be given of a third exemplary embodiment.

Similar parts of the present exemplary embodiment to that of the first exemplary embodiment are allocated the same reference numerals and explanation thereof is omitted. The charging apparatus 14 according to the third exemplary embodiment is shown as charging apparatus 14C.

Figure 9:
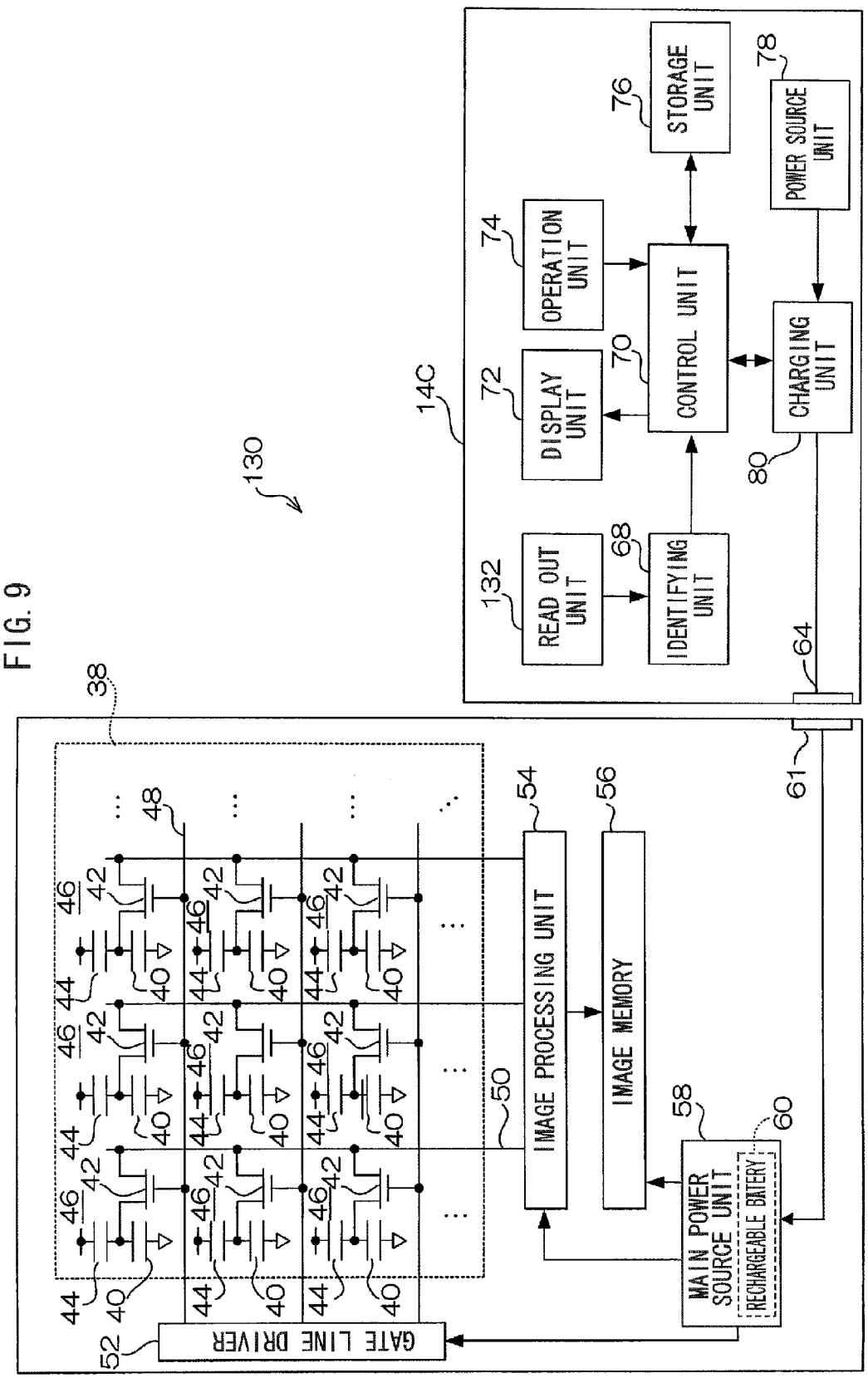
FIG. 9 is a block diagram showing a schematic configuration of a layout of a digital cassette and a digital cassette charging apparatus according to a third exemplary embodiment of the present invention.

The digital cassette charging system 130 according to the present exemplary embodiment shown in FIG. 9 differs from the digital cassette charging system 10 shown in FIG. 3 in that the transmission unit 62 provided to the digital cassette 12 is omitted, and a read out unit 132 of the charging apparatus 14C is provided in place of the receiving unit 66.

Figure 10:
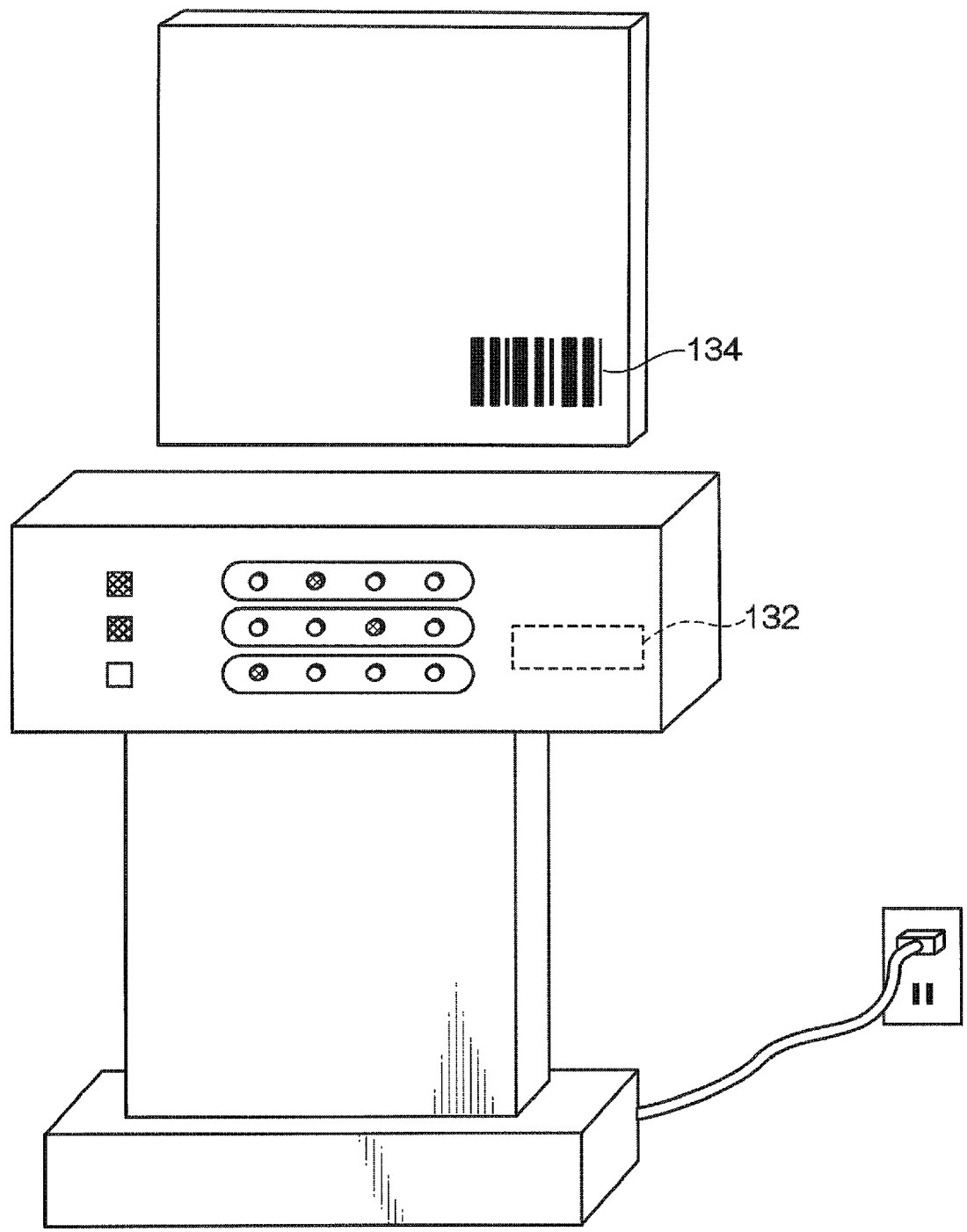
FIG. 10 is a schematic diagram showing a barcode adhered to a digital cassette.

In the present exemplary embodiment, as shown in FIG. 10, a barcode 134 is adhered to the digital cassette 12 representing information indicating the type of digital cassette 12. This barcode 134 is applied so as to be placed at a position in the vicinity of the read out unit 132 when the digital cassette 12 has been loaded into the charging apparatus 14C.

The read out unit 132 reads out the barcode 134 adhered to the digital cassette 12, and outputs the information read out to the identifying unit 68.

The identifying unit 68 has information representing correspondence relationships, between the type of digital cassette and the information of the barcode, stored in a non-illustrated internal memory, and the type of digital cassette is identified from these correspondence relationships, according to the information of the barcode that has been input from the read out unit 132.

In the processing routine of the charging processing according to the present exemplary embodiment, only the processing performed at step 102 to identify the type of digital cassette 12 differs from the processing of the first exemplary embodiment, and the other processing is similar to that of the first exemplary embodiment and explanation thereof will be omitted.

In step 102, first the barcode 134 adhered to the digital cassette 12 is read out by the read out unit 132, and this information is output to the identifying unit 68. The identifying unit 68 then identifies the type of digital cassette corresponding the information of the barcode 134, which has been input from the read out unit 132, based on correspondence relationships stored in a non-illustrated internal memory, between the type of digital cassette and the barcode information.

As a method for identifying the type of digital cassette other than the above method, configuration may be made by providing a photo-interpreter to the read out unit 132, and identifying the type of digital cassette based on photo detection results of the photo-interpreter. Physical indentations and protrusions may be formed to the digital cassette 12, such that the type of digital cassette 12 can be identified in the read out unit 132, by identification based on reflected light when light is irradiated onto the indentation and protrusion portion of the digital cassette.

Explanation will now be given of a fourth exemplary embodiment.

Similar parts of the present exemplary embodiment to that of the first exemplary embodiment are allocated the same reference numerals and explanation thereof is omitted. The charging apparatus 14 according to the fourth exemplary embodiment is shown as charging apparatus 14D.

Figure 11:
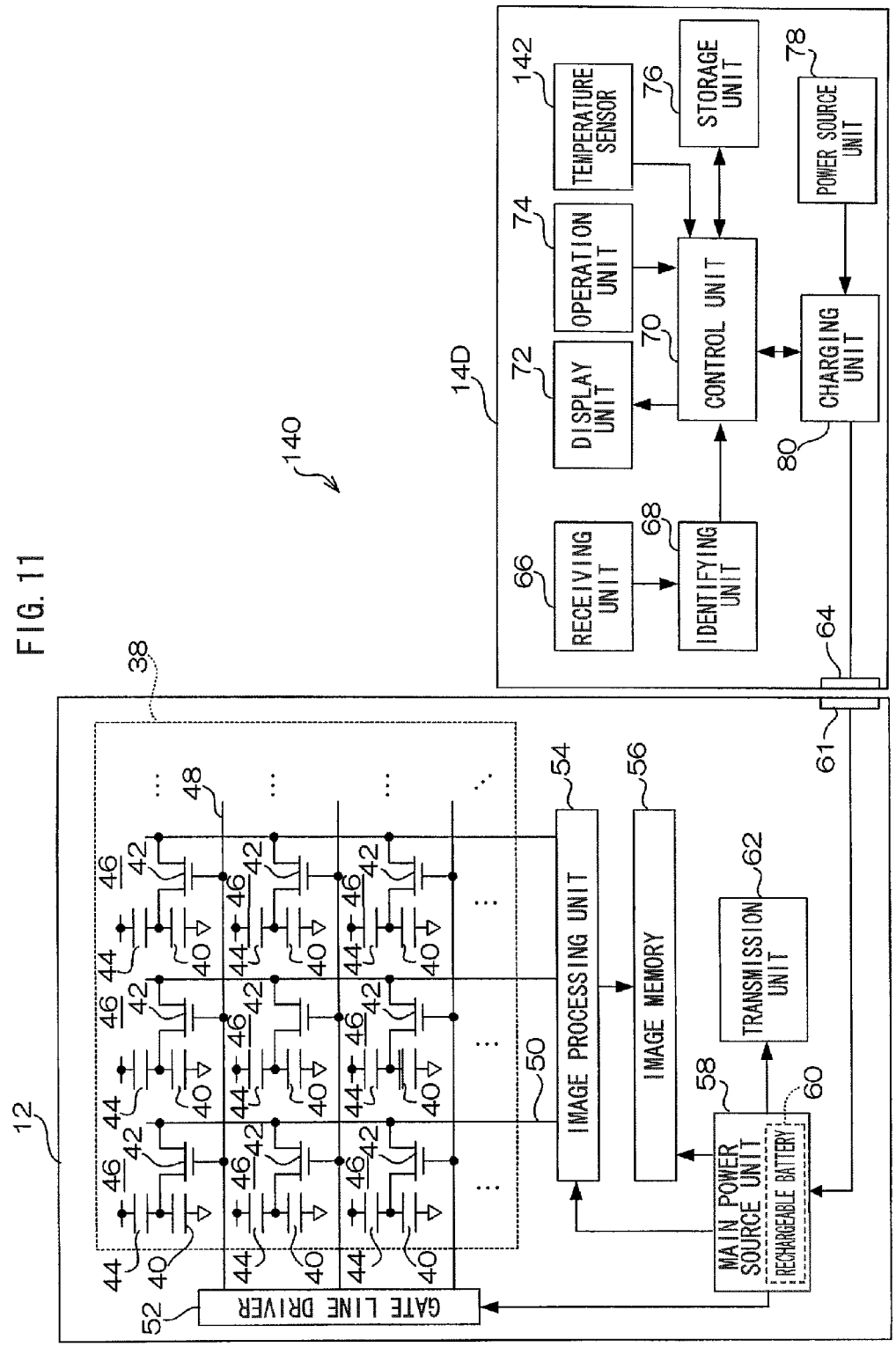
FIG. 11 is a block diagram showing a schematic configuration of a layout of a digital cassette and a digital cassette charging apparatus according to a fourth exemplary

The charging apparatus 14D of a digital cassette charging system 140 according to the present exemplary embodiment, shown in FIG. 11, differs from that of the first exemplary embodiment in that a temperature sensor 142 is provided to the charging apparatus 14A of the digital cassette charging system 10 shown in FIG. 3, for detecting the temperature in the vicinity of the digital cassette when a digital cassette is loaded into the charging apparatus 14, and as shown in FIG. 12, information 144 stored in the storage unit 76, representing correspondence relationships between the type of digital cassette and the charging profile information, includes charging profile information for each temperature.

In the example shown in FIG. 12, the information 144 stored in the storage unit 76 is not a single charging profile corresponding to each of the rechargeable batteries, and instead the charging profiles include charging profiles of a predetermined number of types (in this example at 0 degree C., 20 degree C., 40 degree C.) such that the optimum charging profile can be selected according the temperature in the vicinity of the digital cassette 12 when loaded into the charging apparatus 14D.

Figure 13:
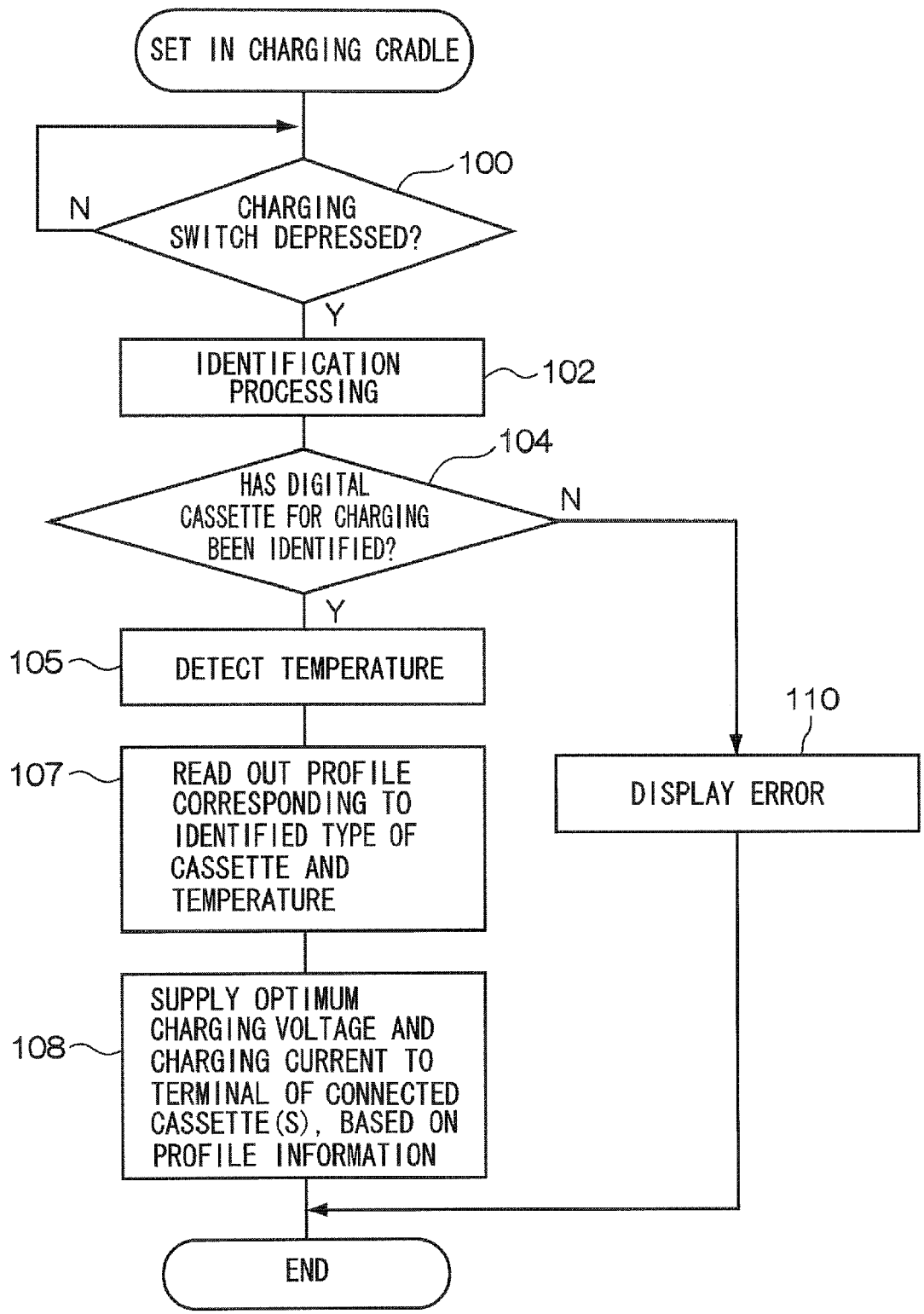
FIG. 13 is a flow chart showing processing flow in charging according to the fourth exemplary embodiment.

Explanation will now be given of the processing routine of the charging processing according to the present exemplary embodiment, with reference to FIG. 13. Processing that is similar to that performed in FIG. 6 is allocated the same reference numeral and explanation thereof will be omitted.

Figure 6:
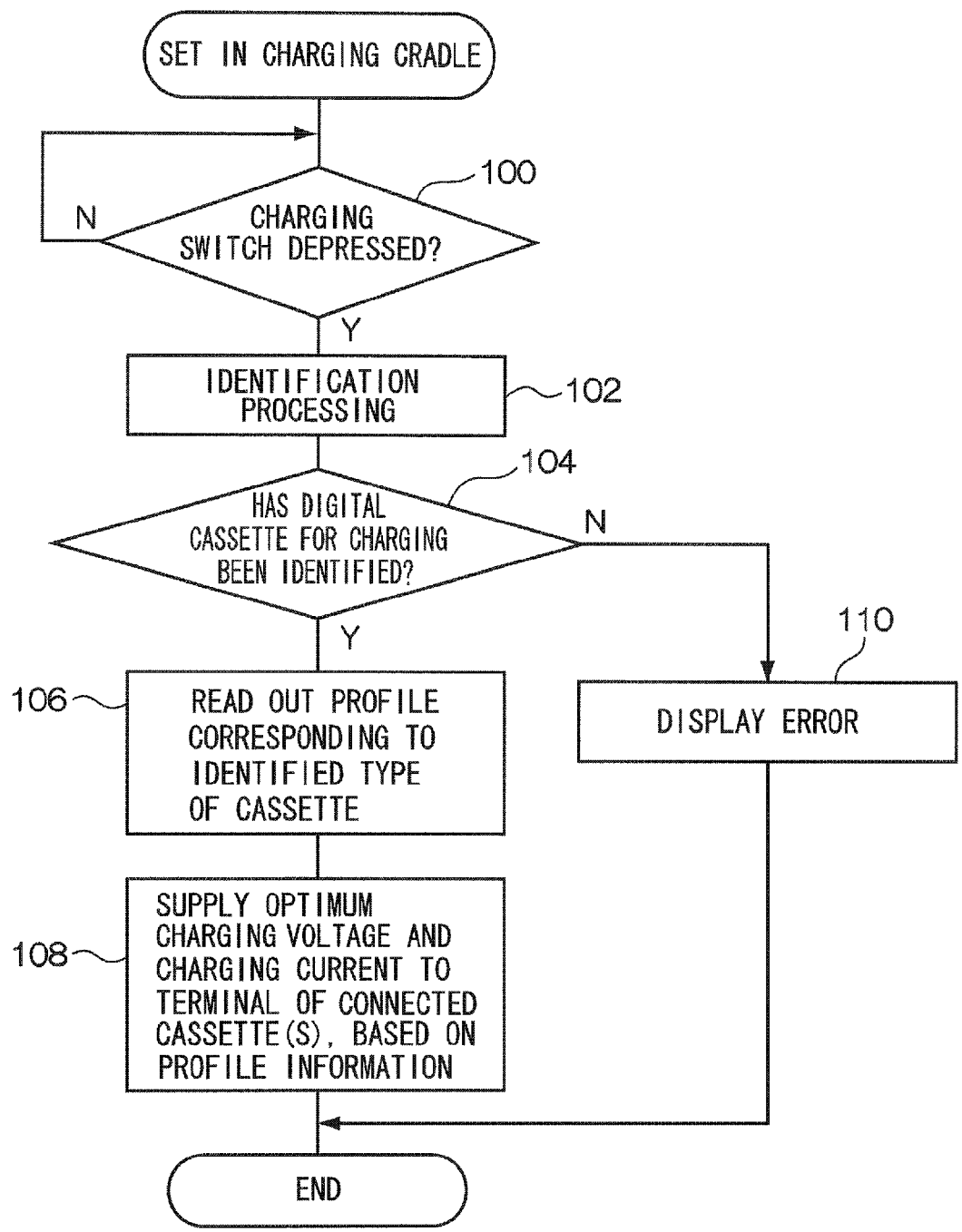
FIG. 6 is a flow chart showing processing flow in charging according to the first exemplary embodiment.

Steps 100 to 104, and step 110 are similar to that of FIG. 6.

The controller 70 is input at step 105 with the temperature that has been detected by the temperature sensor 142.

At step 107, the optimum charging profile is read out from the storage unit 76, corresponding to the type of digital cassette 12 identified at step 104 and to the temperature detected by the temperature sensor 142. When there are plural digital cassettes 12 loaded then the optimum charging profile for each of the digital cassettes 12 and temperatures is read out from the storage unit 76. At step 108, the voltage value and the current value at the start of charging are decided, based on the read-out optimum charging profile and on the present capacity of the rechargeable battery 60, in a similar manner to as in FIG. 6, and the charging unit 80 is controlled so as to start charging the rechargeable battery 60 of the loaded digital cassette 12.

As explained above, according to the digital cassette charging system 140 of the fourth exemplary embodiment, plural types of rechargeable battery can be appropriately charged at the same time according to the temperature of the digital cassettes 12, by configuration with the provision of the temperature sensor and storing in advance charging profiles corresponding to plural types of rechargeable battery of the digital cassettes 12 and to plural temperatures.

In the present exemplary embodiment, explanation has been given of a case in which a temperature sensor is proved to the digital cassette charging system described in the first exemplary embodiment, however, a temperature sensor may be provided to the digital cassette charging systems of the second or third exemplary embodiments.

Explanation will now be given of a fifth exemplary embodiment.

Similar parts of the present exemplary embodiment to that of the first exemplary embodiment are allocated the same reference numerals and explanation thereof is omitted.

Figures 14A, 14B:
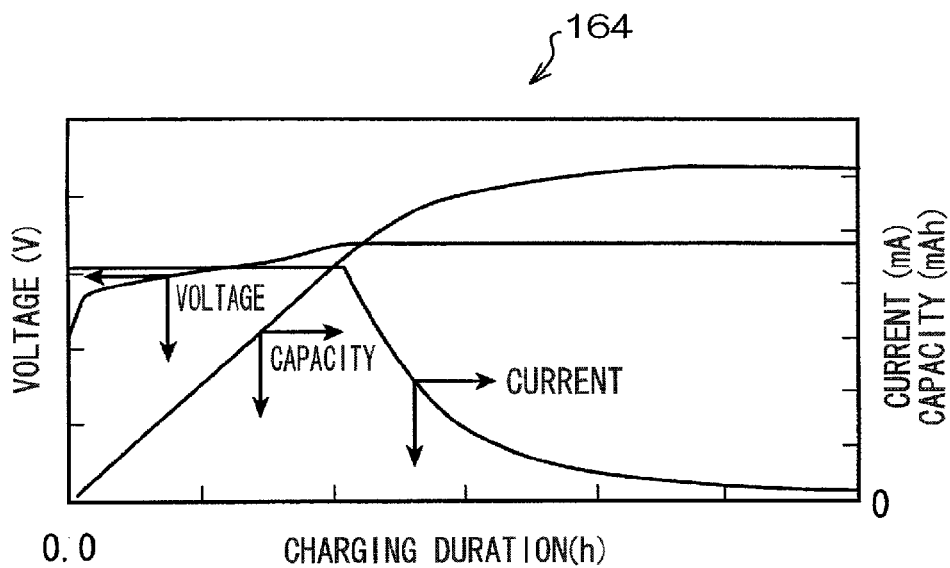
FIG. 14A is a schematic diagram showing types of digital cassette according to the fifth exemplary embodiment and an example of data structure for basic charging profiles.
FIG. 14B is a schematic diagram showing types of digital cassette according to the fifth exemplary embodiment and an example of data structure for basic charging profiles.

The configuration of the digital cassette charging system of the present exemplary embodiment is similar to that shown in FIG. 3, however it differs from the first exemplary embodiment in the respect that there is only a single basic charging profile 164 stored in the storage unit 76, like the one shown in FIG. 14B, and in the respect that there is information 162 representing correspondence relationships between optimum voltage values for the charging voltage, optimum charging currents for the charging current, and capacity of the rechargeable batteries, computed in advance for each of the type of digital cassette 12 and each of the rechargeable batteries, as shown in FIG. 14A, stored in the storage unit 76. Note that there is no limitation to the configuration shown in FIG. 3, and the configuration shown in FIG. 7, FIG. 9, and FIG. 11 are also applicable.

Explanation will now be given of the maximum voltage values and maximum current values of battery packs in which plural rechargeable batteries are packaged.

Below, for example, a case is considered where lithium ion batteries having a maximum voltage value of 4.2 V and a maximum current value of 1715 mA for a single rechargeable battery are used, and the battery pack of the digital cassette 12A is made up with four lithium ion batteries, 2 parallel sets of 2 batteries connected in series, the digital cassette 12B is made up from two lithium ion batteries in a set of 2 batteries connected in series, and the digital cassette 12C is made up from six lithium ion batteries as 3 parallel sets of 2 batteries connected in series.

The maximum voltage value of the digital cassette 12A is 8.4V (4.2V×2), and the maximum current value thereof is 3430 mA (1715 mA×2).

The maximum voltage value of the digital cassette 12B is 8.4V (4.2V×2), and the maximum current value thereof is 1715 mA (1715 mA×1).

The maximum voltage value of the digital cassette 12C is 12.6V (4.2V×3), and the maximum current value thereof is 3430 mA (1715 mA×2).

The maximum voltage values and maximum current values are computed in advance from the configuration of the battery pack housed in each of the digital cassettes 12, and the derived values are stored as the information 162 in the storage unit 76.

Consequently, by detecting the type of digital cassette 12, the charging voltage and the charging current can be appropriately controlled for when the battery pack is being charged, based on the information 162 and the basic charging profile 164.

Figure 15:
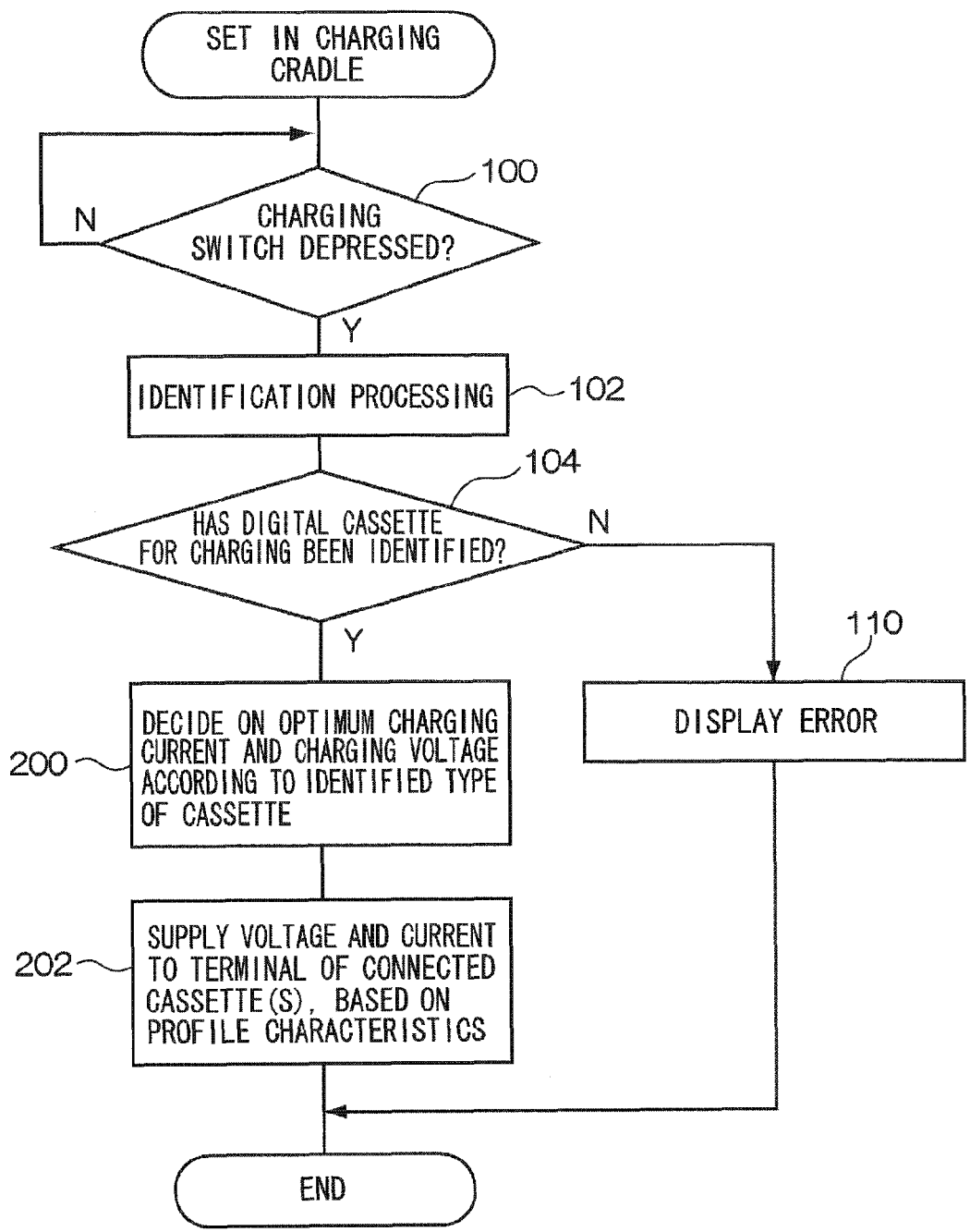
FIG. 15 is a flow chart showing processing flow in charging according to the fifth exemplary embodiment.

Explanation will now be given of the processing routine for charging processing according to the present exemplary embodiment, with reference to FIG. 15. In the processing routine in shown in FIG. 15 only the processing of steps 200 and 202 differ from that of the first exemplary embodiment, and since other parts of the processing are similar to those of the first exemplary embodiment explanation thereof will be omitted.

At step 104, when determination has been made that the type of digital cassette 12 has been identified, the routine proceeds to step 200. At step 200 the information 162 stored in the storage unit 76 is read out corresponding to the type of digital cassette that was identified as the type of digital cassette 12 in step 104, this being the maximum voltage value, the maximum current value and the capacity.

The routine then proceeds to step 202, and the voltage values and charging values from starting charging up to the voltage values and charging values when fully charged are derived, based on the maximum voltage value, maximum current value and capacity read out from the storage unit 76, the basic charging profile 164, and the detected present capacity of the rechargeable battery 60, namely the charging profile is derived, and the voltage values and current values are controlled based on the derived charging profile.

As explained above, in the digital cassette charging system 10 according to the fifth exemplary embodiment configuration is made in which the maximum voltage value, maximum current value and capacity, corresponding to the plural types of rechargeable battery housed in the digital cassettes 12, are stored in advance in the storage unit 76 together with a single basic charging profile. Consequently, plural types of battery pack can be charged at the same time, and the storage capacity required for the storage unit 76 can be decreased in comparison to cases where charging profiles are stored for each type of plural digital cassette.

Configurations of the exemplary embodiments of the present invention are only examples, and obviously the present invention may be appropriately modified within a range not departing from the spirit of the invention.

The flow in processing programs explained for the exemplary embodiments of the present invention are also only examples, and obviously changes may be made to the sequences of each of the steps, step(s) not required may be removed, and additional new steps may be added within a range not departing from the spirit of the invention.

What is claimed is:

1. A digital cassette charging apparatus comprising:
a charging unit loadable with a plurality of types of digital cassettes each comprising an electrical storage device including a rechargeable battery or a capacitor, the charging unit capable of charging the electrical storage devices of the plurality of types of digital cassettes at the same time;
an identification unit for identifying each of the respective types of the plurality of digital cassettes that have been loaded in the charging unit;
a storage unit stored with a charging profile for each of the digital cassettes, the charging profile representing the charging characteristics of the electrical storage device;
and a control unit for reading out from the storage unit the respective charging profile corresponding to the type of digital cassette identified by the identification unit from the plurality of types of digital cassettes, and for controlling the charging unit based on the respective read-out charging profile; wherein
the plurality of types of digital cassettes comprises a first digital cassette and a second digital cassette that are different from one another based on at least one attribute selected from the group consisting of shape, size, maximum voltage value during charging, maximum current value during charging, and capacity during charging; and
the charging profile is a profile representing the relationship among charging duration for various voltage values of charging voltage, current values of charging current, and capacities of charging current, for optimizing the charging by the charging unit.

2. The digital cassette charging apparatus of claim 1, wherein
a barcode indicating the type of the digital cassette is adhered to the digital cassette, and the identification unit comprises a read-out unit for reading out the barcode, and the identification unit identifies each of the respective types of digital cassettes from the plurality of types of digital cassettes based on information of the read-out barcode.

3. The digital cassette charging apparatus of claim 1, wherein
the charging unit comprises a connection portion shaped to correspond to the plurality of digital cassettes, and the identification unit identifies each of the respective types of digital cassettes from the plurality of types of digital cassettes by detecting the digital cassette connected to the connection portion.

4. The digital cassette charging apparatus of claim 1, wherein
the charging unit comprises plural charging electrodes,
the identification unit comprises a contact pattern detection portion for detecting a contact pattern between a charging electrode of the digital cassette and the charging electrodes, and the identification unit identifies each of the respective types of digital cassettes based on the detected contact pattern.

5. The digital cassette charging apparatus of claim 1, wherein
the digital cassette is provided with a transmission unit for transmitting digital cassette information representing the type of the digital cassette; and
the identification unit identifies each of the respective types of digital cassettes loaded into the charging unit based on the digital cassette information transmitted from the transmission unit.

6. The digital cassette charging apparatus of claim 1, wherein the charging profile comprises:
information determined for each of the electrical storage devices of a maximum voltage value, maximum current value, and capacity during charging; and
a basic charging profile determined in advance.

7. The digital cassette charging apparatus of claim 1, further comprising:
a temperature detecting unit for detecting temperature, and charging profiles are stored in the storage unit for each of the digital cassettes, the charging profiles representing charging characteristics for each of a plurality of temperatures of the electrical storage device, wherein
the control unit reads out from storage unit each of the respective charging profiles corresponding to the type of digital cassette identified by the identification unit from the plurality of types of digital cassettes and corresponding to the temperature detected by the temperature detecting unit, and the control unit controls the charging unit based on each of the respective read-out charging profiles.

8. A digital cassette charging system comprising:

a plurality of types of digital cassettes; and a digital cassette charging apparatus for loading with the plurality of types of digital cassettes and charging the digital cassettes at the same time, wherein the digital cassette charging apparatus comprises:

a charging unit loadable with a plurality of types of digital cassettes each comprising an electrical storage device including a rechargeable battery or a capacitor, the charging unit capable of charging the electrical storage devices of the plurality of types of digital cassette at the same time;

an identification unit for identifying each of the respective types of the plurality of digital cassettes loaded in the charging unit;

a storage unit stored with a charging profile for each of the digital cassettes, the charging profile representing the charging characteristics of the electrical storage device; and a control unit for reading out from the storage unit each of the respective charging profiles corresponding to the types of digital cassette identified by the identification unit from the plurality of types of digital cassettes, and for controlling the charging unit based on each of the respective read-out charging profiles, wherein the plurality of types of digital cassettes comprises a first digital cassette and a second digital cassette that are different from one another based on at least one attribute selected from the group consisting of shape, size, maximum voltage value during charging, maximum current value during charging, and capacity during charging; and the charging profile is a profile representing the relationship among charging duration for various voltage values of charging voltage, current values of charging current, and capacities of charging current, for optimizing the charging by the charging unit.

9. A digital cassette charging method comprising:

identifying each of respective types of a plurality of digital cassettes loaded in a charging unit loadable with a plurality of types of digital cassettes each comprising an electrical storage device including a rechargeable battery or a capacitor, the charging unit capable of charging the electrical storage devices of the plurality of types of digital cassette at the same time;

reading out each respective charging profile corresponding to the identified types of digital cassette from the plurality of digital cassettes, reading out being from a storage unit in which a charging profile representing the charging characteristics of the electrical storage device has been stored for each of the electrical storage devices of the plurality of digital cassettes; and controlling the charging unit based on each of the respective read-out charging profiles, wherein the plurality of types of digital cassettes comprises a first digital cassette and a second digital cassette that are different from one another based on at least one attribute selected from the group consisting of shape, size, maximum voltage value during charging, maximum current value during charging, and capacity during charging; and the charging profile is a profile representing the relationship among charging duration for various voltage values of charging voltage, current values of charging current, and capacities of charging current, for optimizing the charging by the charging unit.

* * * * *